(12) United States Patent
    Wesseling

(10) Patent No.: US 12,605,212 B2
(45) Date of Patent: Apr. 21, 2026

(54) SYSTEMS AND METHODS OF DETERMINING LIGAMENT ATTACHMENT AREAS WITH RESPECT TO THE LOCATION OF A ROTATIONAL AXIS OF A JOINT IMPLANT

(71) Applicant: Materialise NV, Leuven (BE)

(72) Inventor: Mariska Wesseling, Leuven (BE)

(73) Assignee: Materialise N.V., Leuven (BE)

( * ) Notice: Subject to any disclaimer, the term of this patent is extended or adjusted under 35 U.S.C. 154(b) by 980 days.

(21) Appl. No.: 17/807,359

(22) Filed: Jun. 16, 2022

(65) Prior Publication Data

US 2022/0313361 A1 Oct. 6, 2022

Related U.S. Application Data

(63) Continuation of application No. PCT/US2020/064659, filed on Dec. 11, 2020.

(60) Provisional application No. 62/951,489, filed on Dec. 20, 2019.

(51) Int. Cl.
    *A61B 34/10* (2016.01)
    *A61B 34/20* (2016.01)
    *A61F 2/38* (2006.01)

(52) U.S. Cl.
    CPC .............. *A61B 34/10* (2016.02); *A61B 34/20* (2016.02); *A61F 2/38* (2013.01); *A61B 2034/105* (2016.02)

(58) Field of Classification Search
    CPC ... A61B 34/10; A61B 34/20; A61B 2034/105; A61F 2/38
    See application file for complete search history.

(56) References Cited

U.S. PATENT DOCUMENTS

| | | | |
|---|---|---|---|
| 2005/0119661 A1 | 6/2005 | Hodgson et al. | |
| 2010/0298894 A1* | 11/2010 | Bojarski | A61B 34/10 |
| | | | 606/86 R |
| 2019/0159848 A1 | 5/2019 | Quaid et al. | |

FOREIGN PATENT DOCUMENTS

| | | |
|---|---|---|
| WO | 2013101753 A1 | 7/2013 |
| WO | 2017151863 A1 | 9/2017 |
| WO | 2020139711 A1 | 7/2020 |

OTHER PUBLICATIONS

Examination Report of Australian Patent Application No. 2020407397, dated Dec. 19, 2025, 5 pages, IP Australia.

* cited by examiner

*Primary Examiner* — Bijan Mapar
(74) *Attorney, Agent, or Firm* — Dinsmore & Shohl LLP

(57) ABSTRACT

Systems and methods of determining ligament attachment areas with respect to the location of a rotational axis of a joint implant are disclosed. Certain embodiments provide a computer-implemented method of evaluating placement of a joint implant with respect to a joint. The method includes determining one or more ligament attachment regions of the joint. The method further includes determining one or more rotational axes of the joint implant. The method further includes determining a position of the joint implant relative to the joint. The method further includes determining whether the one or more rotational axes align with the one or more ligament attachment regions when the joint implant is at the position. The method further includes displaying to a user an indication of whether the one or more rotational axes align with the one or more ligament attachment regions when the joint implant is at the position.

18 Claims, 7 Drawing Sheets

400

402

OBTAIN DEPICTION OF JOINT

404

IDENTIFY LIGAMENT ATTACHMENT REGION

406

DETERMINE ROTATIONAL AXIS OF JOINT IMPLANT

408

DISPLAY JOINT AND JOINT IMPLANT

414

DETERMINE RELATIVE POSITION OF ROTATIONAL AXIS WITH RESPECT TO LIGAMENT ATTACHMENT REGION

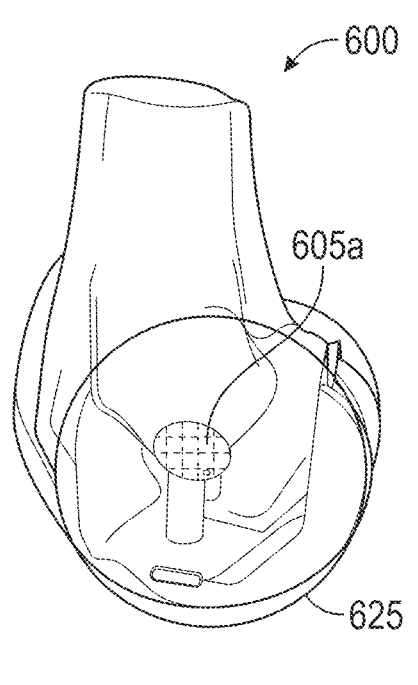
FIG. 6A
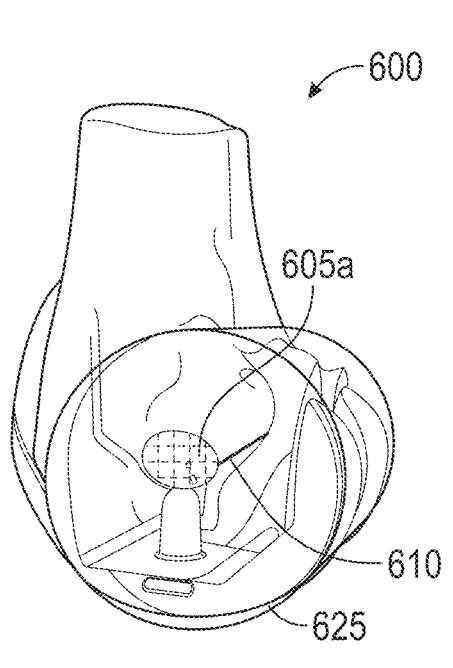
FIG. 6C
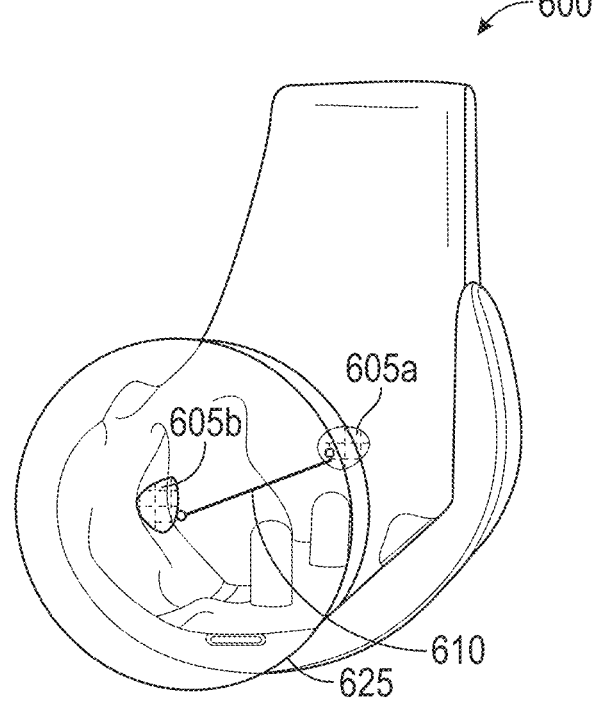
FIG. 6B
FIG. 6D

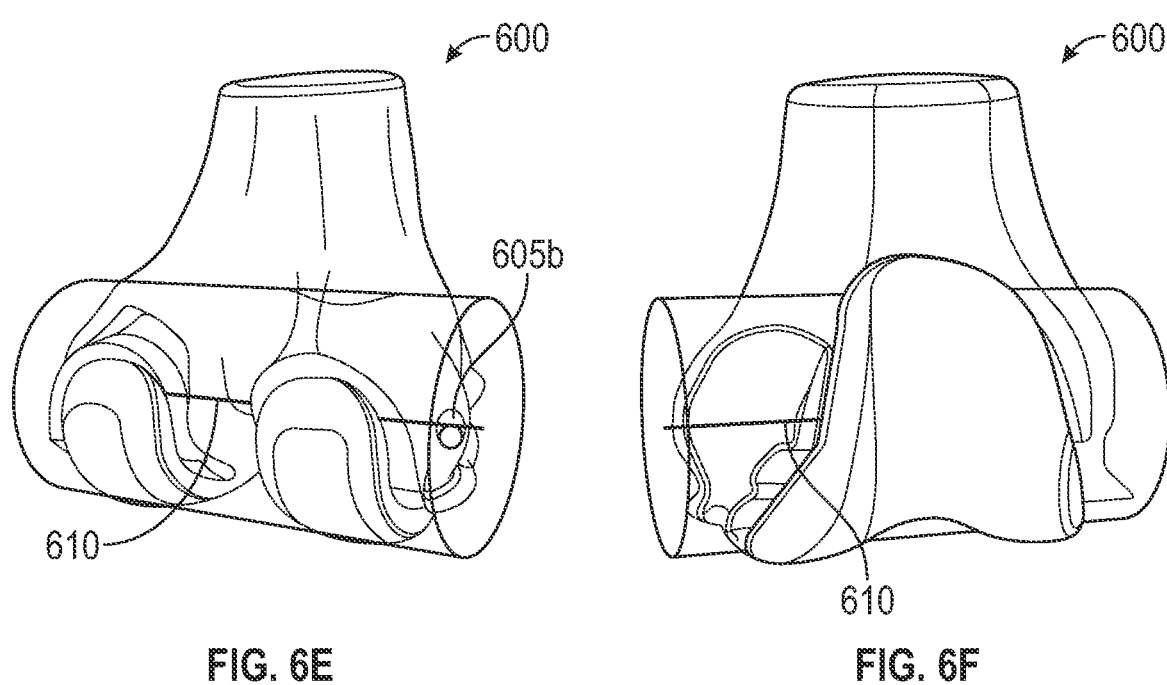
FIG. 6E
FIG. 6F
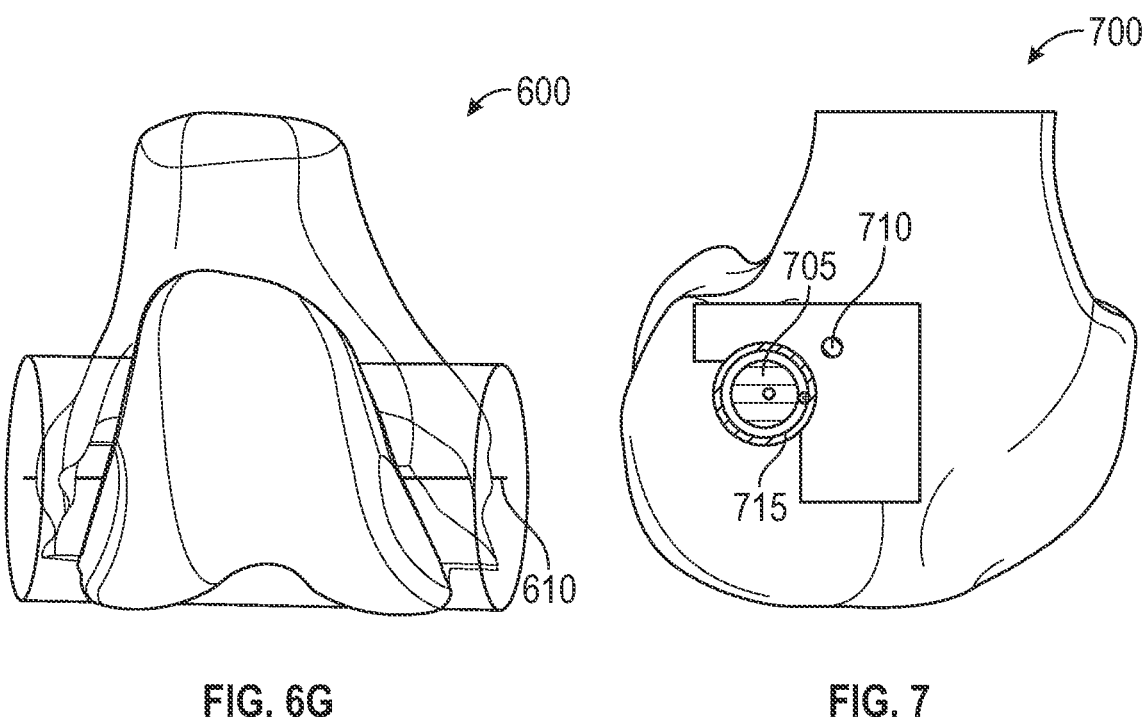
FIG. 6G
FIG. 7

SYSTEMS AND METHODS OF DETERMINING LIGAMENT ATTACHMENT AREAS WITH RESPECT TO THE LOCATION OF A ROTATIONAL AXIS OF A JOINT IMPLANT

CROSS-REFERENCE TO RELATED APPLICATIONS

This application is a continuation of International Application No. PCT/US2020/064659, filed Dec. 11, 2020, which claims the benefit of and priority to U.S. Provisional Patent Application No. 62/951,489, filed Dec. 20, 2019. The entire contents of each of these applications are incorporated herein by reference.

BACKGROUND OF THE INVENTION

Field of the Invention

This application relates to pre-operative planning for surgery. In some aspects, this application relates specifically to systems and methods for using medical imaging and/or data in pre-operative planning for joint implant surgery.

Description of the Related Technology

Conventional pre-operative planning techniques for joint implant surgery do not provide information regarding the soft tissue around the joint for which an implant is to be surgically implanted. For example, in total knee arthroplasty (TKA) surgery, conventional pre-operative planning techniques do not provide any information regarding the soft tissue around the knee joint. Rather, conventional TKA typically aims to merely restore an overall neutral leg alignment following a mechanical alignment, such that, after the implant is surgically implanted, a line going from the center of the hip joint to the center of the ankle joint passes through the center of the replaced knee.

However, such alignment in conventional TKA surgery can cause stresses and/or strains in the ligaments of the joint, as such alignment may not correspond to the pre-operative alignment and function of the knee. For example, such alignment may cause ligaments to be stretched in different directions and/or further than during normal movement of the knee. In another example, such alignment may cause ligaments to be lax, which may cause instability. In particular, soft tissue around a joint can affect the movement and stability of the joint, and the alignment in conventional TKA does not account for this. Accordingly, improved techniques for pre-operative planning for joint implant surgery are desirable.

SUMMARY

Certain embodiments provide a computer-implemented method of evaluating placement of a joint implant with respect to a joint. The method includes determining one or more ligament attachment regions of the joint. The method further includes determining one or more rotational axes of the joint implant. The method further includes determining a position of the joint implant relative to the joint. The method further includes determining whether the one or more rotational axes align with the one or more ligament attachment regions when the joint implant is at the position. The method further includes displaying to a user an indication of whether the one or more rotational axes align with the one or more ligament attachment regions when the joint implant is at the position.

Certain embodiments provide a computer-implemented method of evaluating placement of a joint implant with respect to a joint as part of a joint repair system. The joint repair system may be a joint replacement system. The method includes determining one or more ligaments attaching to a first bone and to a second bone of a joint. The method includes determining one or more ligament attachment regions of the joint. The method further includes determining one or more rotational axes of the joint implant. The method further includes determining a position of the joint implant relative to the joint. The method further includes determining whether the one or more rotational axes align with the one or more ligament attachment regions when the joint implant is at the position. The method further includes displaying to a user an indication of whether the one or more rotational axes align with the one or more ligament attachment regions when the joint implant is at the position.

Certain embodiments provide a non-transitory computer-readable medium having computer-executable instructions stored thereon, which, when executed by a processor of a computing device, cause the computing device to perform a method of evaluating placement of a joint implant with respect to a joint, according to any one or more of the embodiments described herein.

Certain embodiments provide a computing device comprising a memory and a processor configured to perform a method of evaluating placement of a joint implant with respect to a joint, according to any one or more of the embodiments described herein.

BRIEF DESCRIPTION OF THE DRAWINGS

FIGS. 6A-6G illustrate an example of a visualization of a joint implant with respect to a joint from various angles, according to certain embodiments.

FIG. 7 depicts an example visualization of a joint used to determine the location of the rotational axis of the femoral component with respect to the collateral ligament attachment regions, according to certain embodiments.

DETAILED DESCRIPTION OF CERTAIN INVENTIVE EMBODIMENTS

Figure 1B:
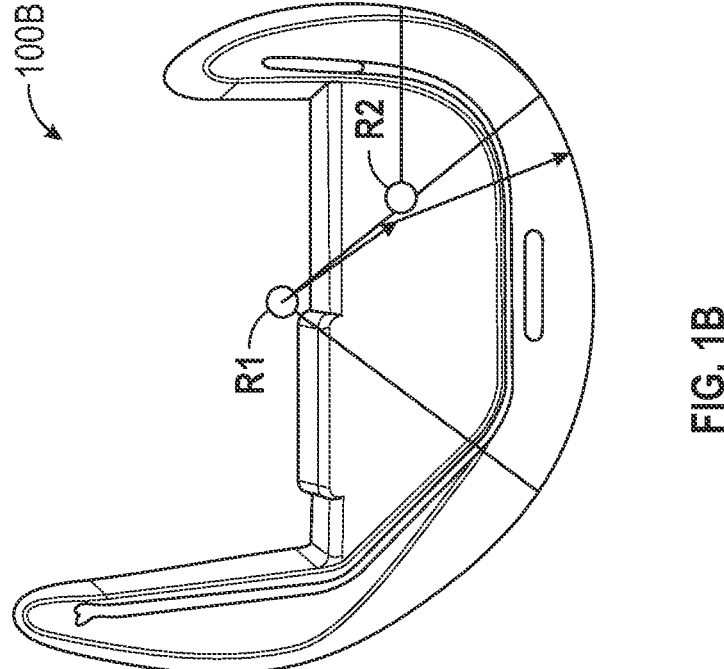
FIGS. 1A and 1B illustrate examples of femoral components of a TKA implant.

Certain embodiments herein provide systems and methods for determining ligament attachment areas with respect to the location of a rotational axis of a joint implant. Such embodiments may be advantageously used during pre-operative planning for joint implant surgery. For example, such systems and methods can be used to beneficially determine whether for a proposed location for implantation of a joint implant in a patient anatomy, one or more rotational axes of the joint implant fall within (or align with) or outside of (or do not align with) one or more ligament attachment areas. If the one or more rotational axes of the joint implant fall outside of the one or more ligament attachment areas, the proposed location of the joint implant may cause additional stresses and/or strains on the ligaments, possibly requiring ligament releases during surgery, or laxity resulting in instability. Accordingly, the proposed location may be revised, such that for the revised location the one or more rotational axes of the joint implant fall within the one or more ligament attachment areas, thereby reducing stresses and/or strains on the ligaments, or reducing laxity thereby avoiding instability.

As discussed, conventional pre-operative planning techniques for joint implant surgery do not provide information regarding the soft tissue (e.g., ligaments) around the joint for which an implant is to be surgically implanted, and present a technical problem as to how to properly account for soft tissue in joint implant surgery. The embodiments herein provide a specific technical solution that provides techniques to account for soft tissue in joint implant surgery by determining if one or more rotational axes of the joint implant fall within one or more ligament attachment areas, so as to reduce stresses and/or strains on the ligaments, reduce the need for ligament releases during surgery, or reduce laxity thereby avoiding instability. As will be discussed further, this provides a technical solution that is not provided by other techniques.

It should also be noted that in certain embodiments, one or more of the methods described herein is a computer-implemented method. For example, computer-based images and/or 3D geometries used in certain embodiments necessarily need to be generated on a computing device and the generation of such images and/or 3D geometries is a computer centric problem. In particular, such images cannot be generated mentally or by a human alone without a computing device. Further, certain steps may be performed automatically, manually by a user of a computing device, or partially manually and partially automatically such as based on input from a user of a computing device. Further, in certain embodiments, a user may be a person, such as a clinician, engineer, technician, medical professional, non-medical professional, etc., that may use a computing device to, or the computing device itself may automatically perform one or more steps of one or more methods described herein.

Certain embodiments are described herein with respect to TKA, and the use of a TKA implant. For example, certain embodiments are described with respect to a femoral component of a TKA implant, and in particular, determining whether one or more axes of rotation of the femoral component align with the attachment regions of the lateral collateral ligament (LCL) and medial collateral ligament (MCL) on the femur. For example, in certain aspects, the MCL (and LCL in the first part of the flexion movement) are expected to behave isometrically during knee flexion, so the axes of rotation should align with the attachment regions of the LCL and MCL on the femur. However, it should be noted that such description with respect to a TKA is merely illustrative, and the embodiments of techniques discussed herein may also be used for other types of joint implant surgery, using other types of implants, such as for other joints and corresponding ligaments. For example, the embodiments may be used for joint implant surgery of one or more of an elbow, ankle, finger joint, toe joint, hip, shoulder, wrist, vertebral joint, etc. Further, in certain aspects the implant may be an off the shelf implant. In certain aspects the implant may be a patient-specific implant.

As discussed, embodiments herein provide a technical solution that is not provided by other techniques. For example, in some techniques, soft tissue balancing may be performed following intra-operative measurements (force measurements, gap measurements, etc.), however, such techniques do not specifically provide for determining if one or more rotational axes of the joint implant fall within one or more ligament attachment areas, so as to reduce stresses and/or strains on the ligaments, or reduce laxity thereby avoiding instability. In another example, kinematic modelling and kinematic alignment to preserve soft tissue has been proposed (Howell, Stephen M., et al. 2015. Does varus alignment adversely affect implant survival and function six years after kinematically aligned total knee arthroplasty? International Orthopaedics (SICOT) Volume 39, 2117-2124; An, Vincent V. G. et al. 2019. Kinematic alignment is bone and soft tissue preserving compared to mechanical alignment in total knee arthroplasty. The Knee, Volume 26, Issue 2, 466-476; Twiggs, Joshua G. et al. 2018. Patient-Specific Simulated Dynamics after Total Knee Arthroplasty Correlate with Patient-Reported Outcomes. The Journal of Arthroplasty, Volume 33, Issue 9, 2843-2850), however, such techniques do not specifically provide for determining if one or more rotational axes of the joint implant fall within one or more ligament attachment areas, so as to reduce stresses and/or strains on the ligaments, avoid ligament releases, or reduce laxity thereby avoiding instability.

Some papers describe the accuracy of segmentation of knee ligaments, however, not in relation to the orientation of a joint implant (Innocenti B, et al. 2016. How accurate and reproducible are the identification of cruciate and collateral ligament insertions using MRI? Knee, Volume 23, Issue 4, 575-581; Rachmat H. H. et al. 2014. Generating finite element models of the knee: How accurately can we determine ligament attachment sites from MRI scans? Medical Engineering & Physics, Volume 36, Issue 6, 701-707), and accordingly do not help to reduce stresses and/or strains on the ligaments, or reduce laxity thereby avoiding instability. One paper describes the location of the joint line (before and after TKA) on the laxity of the ligaments (Luyckx T, et al. 2018. Raising the Joint Line in TKA is associated with Mid-flexion Laxity: A Study in Cadaver Knees. Clin Orthop Relat Res 476:601-611), however, does not specifically provide for determining if one or more rotational axes of the joint implant fall within one or more ligament attachment areas, so as to reduce stresses and/or strains on the ligaments, or reduce laxity thereby avoiding instability.

Anatomical literature describes the location of the attachment regions with respect to bony landmarks. For example, the location of the MCL attachment region is described with respect to three landmarks, i.e. adductor tubercle, gastrocnemius tubercle and medial epicondyle (Liu, Fang, et al. 2010 Morphology of the medial collateral ligament of the knee. Journal of orthopaedic surgery and research, Volume 5, Issue 1, 69). The location of the LCL area is described with respect to the lateral epicondyle (Brinkman, J-M., et al. 2005. The insertion geometry of the posterolateral corner of the knee. The Journal of bone and joint surgery. British volume 87, Issue 10, 1364-1368).

Figure 1A:
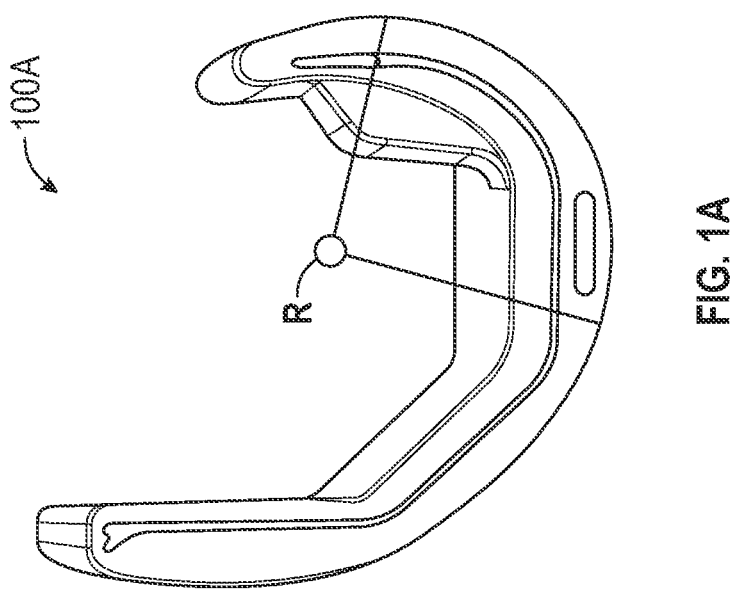

FIGS. 1A and 1B illustrate examples of femoral components of a TKA implant. FIG. 1A illustrates a femoral component of a TKA implant 100A having a single axis of rotation R, and may also be referred to as a "single-radius" implant. As shown, the TKA implant 100A is configured to rotate about the single axis of rotation R throughout the rotation of the TKA implant 100A after implantation, such as throughout flexing of the knee after implantation. In a single-radius TKA implant, the posterior part of the femoral component can be considered circular shaped with a fixed axis of rotation.

A single-radius design of a TKA implant 100A can ensure a constant tension in the collateral ligaments (e.g., MCL and LCL). However, a constant tension in the ligaments may only be possible if the femoral component is positioned such that the axis of rotation is aligned with the ligament attachments, according to the techniques discussed herein.

FIG. 1B illustrates a femoral component of a TKA implant 100B having two axes of rotation R1 and R2, and may also be referred to as a "multi-radius" implant. As shown, the TKA implant 100B is configured to rotate about the axis of rotation R1 for a first portion of the rotation of the TKA implant 100B and rotate about the axis of rotation R2 for a second portion of the rotation of the TKA implant 100B after implantation, such as during flexing of the knee after implantation. It should be noted that a multi-radius implant may also have more than two rotational axes. In a multi-radius TKA implant, a change in location of the axis of rotation occurs towards deep flexion of the knee. The techniques herein can not only help reduce stresses and/or strains for single-radius implants, limit the number of ligament releases, or reduce laxity thereby avoiding instability, but also for multi-radius implants, such as by positioning the multi-radius implant such that one or more of the multiple axes of rotation align with the ligament attachments, according to the techniques discussed herein. It should be noted that the illustrated multi-radius implant is only one example of a multi-radius implant with multiple axes of rotation, and that other implant types may have multiple axes of rotation, such as generally reducing radius, medial pivot, etc.

Certain embodiments provide computer visualization for a user to visualize ligament attachment regions of a joint, together with one or more rotational axes of a joint implant. In certain embodiments, if a rotational axis of a joint implant is positioned outside of a ligament attachment region, a warning may be displayed to the user that the collateral ligaments could be unbalanced. The user can then reposition the joint implant to avoid a rotational axis of the joint implant being positioned outside of a ligament attachment region.

In certain embodiments, the computing device itself may automatically determine or propose a position of a joint implant based on the one or more rotational axes of the joint implant and the ligament attachment regions, such as with or without an initial proposed position by a user. For example, the computing device may position the joint implant such that the one or more rotational axes of the joint implant align with the ligament attachment regions. The computing device may, for example, iteratively try different joint implant positions until a position that meets said criteria is found. The computing device may present the position to a user for approval or for further manipulation by the user.

Figure 2:
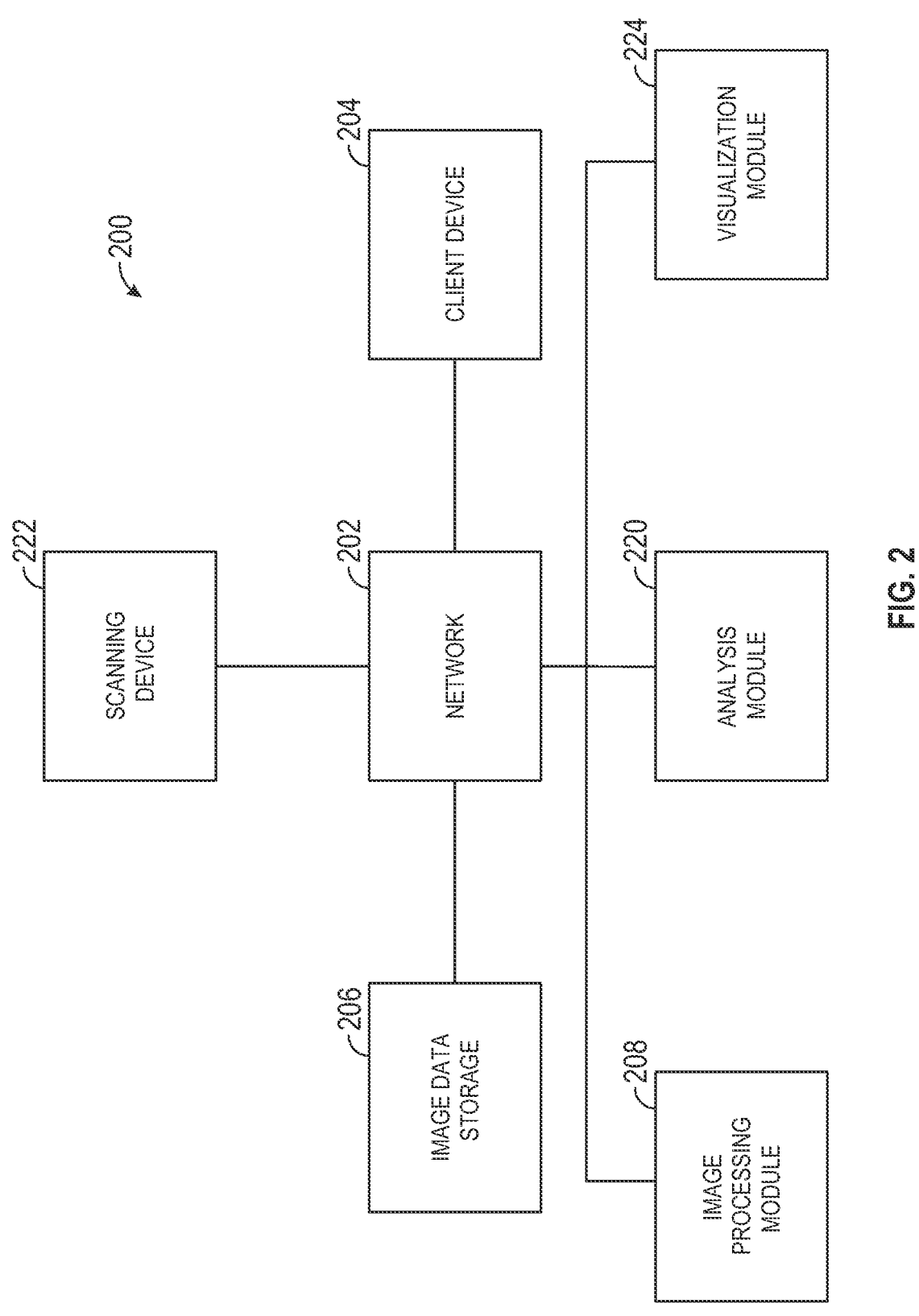
FIG. 2 is a block diagram of one example of a computing environment suitable for practicing various embodiments disclosed herein.

The systems and methods described herein may be implemented in a computing environment comprising one or more computing devices configured to provide various functionalities. FIG. 2 is an example of a computer environment 200 suitable for implementing certain embodiments described herein. The computer environment 200 may include a network 202. The network 202 may take various forms. For example, the network 202 may be a local area network installed at a surgical site. In some embodiments, the network 202 may be a wide area network such as the Internet. In other embodiments, the network 202 may be a combination of local area networks and wide area networks. Typically, the network will allow for secured communications and data to be shared between various computing devices. Among these computing devices are a client device 204. The client device 204 may be a typical personal computer device that runs an off-the-shelf operating systems such as Windows, Mac OS, Linux, Chrome OS, or some other operating system. The client device 204 may have application software installed to allow it to interact via the network 202 with other software stored on various other modules and devices in the computing environment 200. This application software may take the form of a web browser capable of accessing a remote application service. Alternatively, the application software may be a client application installed in the operating system of the client device 204. Client device 204 may also take the form of a specialized computer, specifically designed for medical imaging work. The client device 204 may further take the form of a mobile device or tablet computer configured to communicate via the network 202 and further configured to run one or more software modules to allow a user to perform various methods described herein.

The computer environment 200 may further include image data storage 206. Typically, the image data storage 206 takes the form of a database designed to store image files captured by a scanning device 222 (e.g., X-ray imaging device, MRI, CT, ultrasound, etc.), or other depictions of a joint. These images may be Digital Imaging and Communications in Medicine (DICOM) images, and/or other types of images, volumetric data, 2D, 3D, 4D (3 spatial dimensions and time) depictions, etc., of joints.

In certain aspects, an image may include depictions of one or more markers positioned on a patient while taking the image. For example, physical markers (e.g., radiopaque markers) may be positioned on the skin of a patient, such as at the approximate position of one or more bony landmarks or other 3D geometries. The one or more bony landmarks may include one or more of: femoral condyles, tibial tuberosity, fibular notch, medial condyle of the tibia, patella, medial femoral epicondyle, lateral femoral epicondyle, adductor tubercle, gastrocnemius tubercle, etc. Such positions for placement of markers may be determined, for example, by a user, clinician, etc. The image of the anatomy of the patient, therefore, may include depictions of the one or more markers, thereby identifying in the image of the anatomy the approximate position of the one or more bony landmarks.

As discussed herein, 3D geometries (e.g., position(s) of one or more bony landmarks) may be used to approximate the location of ligament attachment regions, such as when used in conjunction with a mapping of the location of ligament attachment regions with respect to 3D geometries (e.g., of bony landmarks) as disclosed in literature as discussed. For example, the position(s) of the one or more bony landmarks, along with the dimensions (e.g., average dimensions for a patient of certain height, weight, etc.) of the ligament attachment regions, may be used along with the mappings discussed in literature, to identify the ligament attachment regions of a patient.

The image data storage 206 may be part of a scanning device 222, or alternatively it may be part of a client computing device 204. The image data storage 206 may also be in a standalone database having dedicated storage optimized for medical image data. The image data store 206 may further include in the same database or a separate database 2-D and or 3-D digital representations/images of designs of joint implants, as further discussed herein. The computer environment 200 may also include a scanning device 222. The scanning device 222 may typically be a medical imaging device which scans/images a patient to create images of their joint and/or volumetric data of the joint.

The scanning device 222 may be configured to create images or depictions of joints. Those images may be stored in the image data storage 206. In certain aspects, the images or depictions such as volumetric data are utilized to create 2D, 3D, or 4D models of the joint (e.g., anatomy of the joint). In certain aspects, the images and/or models may be segmented using known segmenting techniques.

To that end, the computing environment 200 may also include an image processing module 208. The image processing module 208 may be a commercially available image processing software for three-dimensional design and modeling such as the Mimics application from Materialise NV. For example, Mimics can be used to perform segmenting as discussed herein, as well as creation of virtual models of a joint, such as from images and/or volumetric data obtained from scanning device 222 and/or stored in image data storage 206. However, other image processing software may be used. Segmentation is the process of partitioning a digital image into multiple segments (e.g., sets of pixels, also known as image objects). In certain embodiments, the image process module 208 is configured to identify one or more 3D geometries, such as one or more bony landmarks, associated with the joint, such as from images and/or volumetric data obtained from scanning device 222 and/or stored in image data storage 206. In certain embodiments, the digital image is of a joint, and one or more of the image objects are ligament attachment areas (e.g., to bone) and/or one or more ligaments. In certain embodiments, the image processing module 208, or another processing module, such as analysis module 220, may use virtual models to identify other segments, e.g. ligament attachment regions.

The image processing module 208, or another processing module, such as analysis module 220, may further be configured to fit a geometric shape (e.g., cylinder or sphere) through a joint implant as part of defining a rotational axis of the joint implant as further discussed herein. For example, the image processing module 208 or analysis module 220 may also include the 3-matic component of the Mimics application from Materialise NV configured to fit a geometric shape to an object, such as the joint implant. The image processing module 208 may take the form of computer software, hardware, or a combination of both. In some embodiments, the image processing module 208 may be provided via a web-based network application that is accessed by a computer over the network (such as client device 204, for example). Alternatively, the image processing module may be a software application that is installed directly on the client device 204, and accesses image data storage 206 via the network 202. In general, the image processing module 208 may be any combination of software and/or hardware located within the computing environment 200 which provides image processing capabilities on the image data stored within the image data storage 206.

The computing environment also may include an analysis module 220 ("analysis module"). The analysis module 220 may be software that is complementary to and/or bundled with the image processing module 208. The analysis module 220 may be an application configured to determine ligament attachment areas with respect to the location of a rotational axis of a joint implant according to the techniques discussed herein. For example, the analysis module 220 may be configured to determine whether for a proposed location for implantation of a joint implant in a patient anatomy, one or more rotational axes of the joint implant fall within (or align with) or outside of (or do not align with) one or more ligament attachment areas. As with the image processing module 208, the analysis module 220 may be a network-based application which is accessed via a web browser by one or more client devices 204. It may also be a native application installed into the operating system of a computer such as, client device 204 for example. In still other embodiments, the analysis module 220 may be a network application which is run as a client/server implementation.

The computing environment also may include a visualization module 224. The visualization module 224 may be software that is complementary to and/or bundled with the image processing module 208. The visualization module 224 may be an application configured to provide different visualizations of objects. For example, visualization module 224 may cause one or more joints and/or joint implants to be displayed on a display of a computing device, such as client device 204, by rendering images for display. Visualization module 224, as will be discussed, may render images with different colors, sizes, according to different user interfaces, as schematic or lifelike images, as 2D or 3D models, as wireframe, surface, or volume models, etc. for display. Visualization module 224 may further render images overlaid on top of other images, such as images or renders (e.g., 2D or 3D) of implants on joints and/or illustrating ligaments, as further discussed herein. In certain aspects, the visualization module 224 provides visualization according to a selectable user preference. As with the image processing module 208, the visualization module 224 may be a network-based application which is accessed via a web browser by one or more client devices 204. It may also be a native application installed into the operating system of a computer such as, client device 204 for example. In still other embodiments, the visualization module 224 may be a network application which is run as a client/server implementation. In certain embodiments, the visualization module 224 may further render images and/or virtual models in augmented reality to allow better visualization. In certain aspects, a user may use the augmented reality rendering by the visualization module 224 during surgery or for training purposes. In certain embodiments, the visualization module 224 may further render images and/or 3D models and/or virtual models when used with surgical navigation systems.

Figure 3:
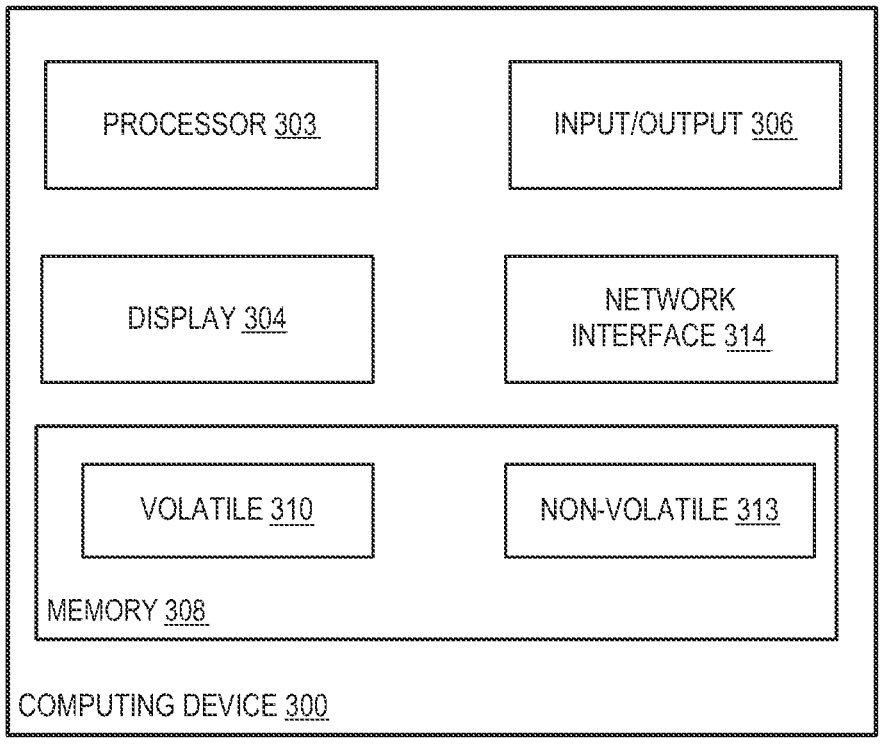
FIG. 3 is a high level system diagram of a computing system that may be used in accordance with one or more embodiments.

Various embodiments of the invention may be implemented using general and/or special purpose computing devices. Turning now to FIG. 3, an example of a computing device 300 suitable for implementing various embodiments of the invention is shown. The computer system 300 may generally take the form of computer hardware configured to execute certain processes and instructions in accordance with various aspects of one or more embodiments described herein. The computer hardware may be a single computer or it may be multiple computers configured to work together. The computing device 300 includes a processor 303. The processor 303 may be one or more standard personal computer processor such as those designed and/or distributed by Intel, Advanced Micro Devices, Apple, or ARM. The processor 303 may also be a more specialized processor designed specifically for image processing and/or analysis. The computing device 300 may also include a display 304. The display 304 may be a standard computer monitor, such as an LCD monitor as is well known. The display 304 may also take the form of a display integrated into the body of the computing device, for example as with an all-in-one computing device or a tablet computer.

The computing device 300 may also include input/output devices 306. These may include standard peripherals such as keyboards, mice, printers, and other basic I/O software and hardware. The computing device 300 may further include memory 308. The memory 308 may take various forms. For example, the memory 308 may include volatile memory 310. The volatile memory 310 may be some form of random access memory, and may be generally configured to load executable software modules into memory so that the software modules may be executed by the processor 303 in a manner well known in the art. The software modules may be stored in a nonvolatile memory 313. The non-volatile memory 313 may take the form of a hard disk drive, a flash memory, a solid state hard drive or some other form of non-volatile memory. The non-volatile memory 313 may also be used to store non-executable data, such database files and the like.

The computer device 300 also may include a network interface 314. The network interface may take the form of a network interface card and its corresponding software drivers and/or firmware configured to provide the system 300 with access to a network (such as the Internet, for example). The network interface card 314 may be configured to access various different types of networks, such as those described above in connection with FIG. 2. For example the network interface card 314 may be configured to access private networks that are not publicly accessible. The network interface card 314 may also be configured to access wireless networks such using wireless data transfer technologies such as EVDO, WiMax, or LTE network. Although a single network interface 314 is shown in FIG. 3, multiple network interface cards 314 may be present in order to access different types of networks. In addition, a single network interface card 314 may be configured to allow access to multiple different types of networks.

In general, the computing environment 300 shown in FIG. 3 may generally include one, a few, or many different types of computing devices 300 which work together to carry out various embodiments described below. A skilled artisan will readily appreciate that various different types of computing devices and network configurations may be implemented to carry out the inventive systems and methods disclosed herein.

Figure 4:
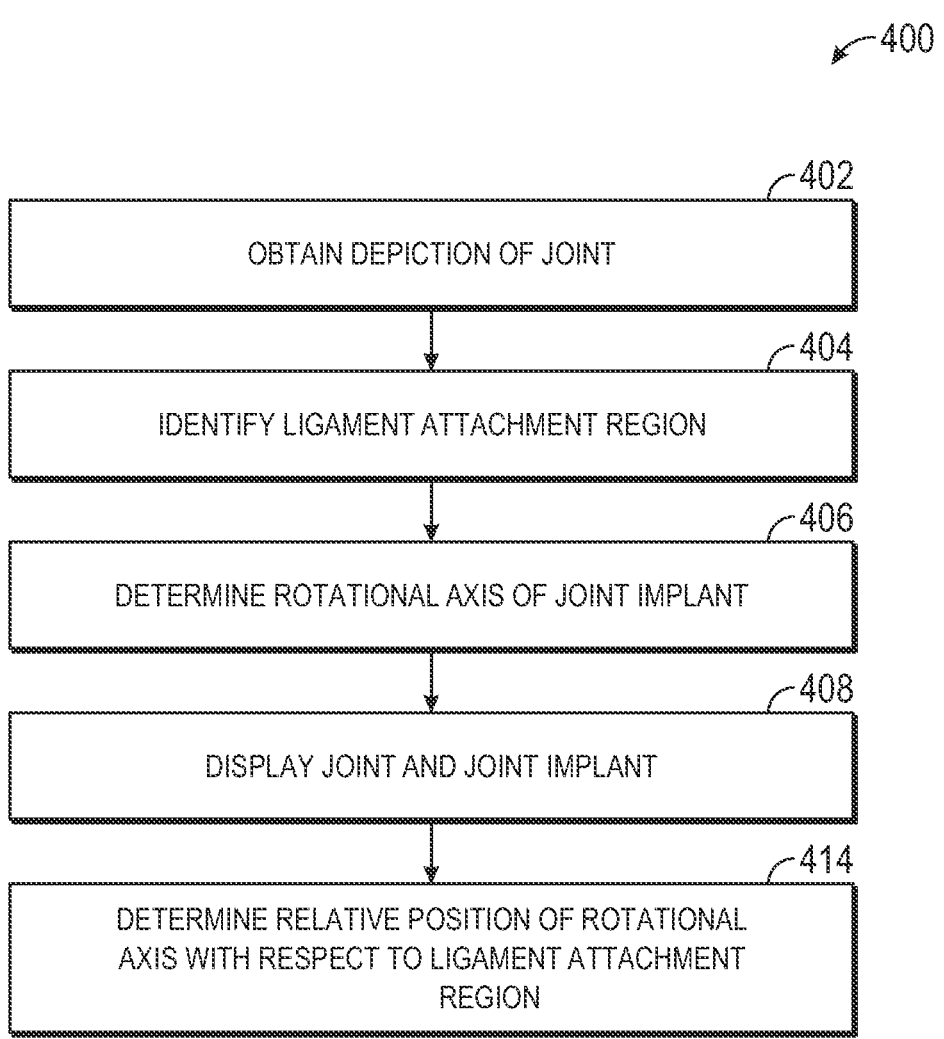
FIG. 4 illustrates a flow chart showing a process for evaluating placement of a joint implant with respect to a joint, according to certain embodiments.

FIG. 4 illustrates a flow chart showing a process 400 for evaluating placement of a joint implant with respect to a joint, according to certain embodiments. It should be noted that in certain embodiments, process 400 is a computer-implemented process. Further, certain blocks may be performed automatically, manually by a user of a computing device, or partially manually and partially automatically such as based on input from a user of a computing device.

Process 400 begins at block 402, wherein one or more depictions of the joint (e.g., a portion of the joint) are obtained. In certain embodiments, the one or more depictions are of a knee joint. The one or more depictions may be obtained, for example, from a scanning device 222, image processing module 208, and/or image data store 206, as discussed. In certain aspects, the one or more depictions of the joint comprise one or more images and/or volumetric data of the joint, such as obtained by scanning device 222.

Further, at block 404, one or more ligament attachment regions, such as where one or more ligaments attach to a bone, are identified in the depiction of the joint.

In certain aspects, the one or more images and/or volumetric data of the joint are segmented to identify the one or more ligament attachment regions. For example, the images and/or volumetric data are segmented, such as using image processing module 208, to identify ligament attachment regions, such as an LCL attachment region and an MCL attachment region, where the LCL and MCL attach to the femur. In certain aspects, identifying a ligament attachment region could be achieved by segmenting both the bone surface (a first anatomical structure) and the ligament (a second anatomical structure) itself, resulting in pixel/voxel masks (a subset of the image pixels/voxels that make up an anatomical structure) representing both structures and then labelling each pixel/voxel of the image that is within a minimum distance of both the voxel mask of the ligament and that the voxel mask of the bone, as being part of the ligament attachment region. In the context of 3D operations such as 3D models, stacked images or stacked masks such pixels may be referred to as voxels, and the terms pixels and voxels may be used interchangeably.

In certain aspects, the trajectory of a ligament in one or more images can be followed to where it inserts in the bone; this are of the bone is then identified as the ligament attachment region. For example, the ligament in the one or more images can be segmented, and the intersection of the extrapolated 3D structure of the ligament and the bone identified as the ligament attachment region.

In certain aspects, the ligament attachment regions may be manually identified in the one or more images.

In certain aspects, the one or more ligament attachment regions can be identified in the depiction of the joint automatically using one or more 3D geometries (e.g., bony landmarks) associated with the joint. For example, as discussed, the one or more bony landmarks may be identified in the one or more images and/or volumetric data (e.g., as identified by markers), may be obtained as position information (e.g., coordinate information, etc.) with respect to the depiction of the joint (e.g., from a clinician, user, etc.), etc. In certain aspects, based on the position of the one or more bony landmarks with relation to the depiction of the joint, and further based on a mapping of the position of the one or more bony landmarks (e.g., such as stored at a computing device and based on descriptions in anatomical literature based on cadaver work) to position(s)/dimension(s) of ligament attachment regions, the one or more ligament attachment regions can be identified. In certain aspects, the mapping may describe the position of a ligament attachment region as a point at certain distances from a bony landmark in specific anatomical directions (e.g. a certain distance posterior to the landmark and a certain distance superior (e.g., proximal) to the landmark). In certain aspects, the mapping may comprise (1) calculating the intersection points of one or more pairs of circles of certain radii, each centered on a bony landmark and projected onto an plane (e.g., a plane parallel to the sagittal plane passing through one of the bony landmarks); (2) for each pair of circles, selecting one of the two resulting intersection points (e.g., the most posterior or inferior point); (3) if more than one pair of circles is used, calculating the centroid of the resulting points; and (4) selecting the point on the 3D geometry of the bone (or on a projection (e.g., perpendicular to the anatomical plane)) that is closest to the resulting centroid (or the resulting intersection point where only one pair of circles is used) as the position of the ligament attachment region. For example, each of the one or more ligament attachment regions may be identified to have a size (e.g., average size based on size, weight, height, etc. of the patient) and a position that is calculated with respect to the position of the one or more bony landmarks in accordance with the mapping. For example, in certain aspects, the size of a ligament attachment region may be determined by the dimensions of an ellipse defined in an specific plane (e.g., a plane parallel to the sagittal plane passing through one of the bony landmarks); the projection of this ellipse onto the surface of the bone, in a direction perpendicular to the plane, determines the attachment region on the bone. Accordingly, certain embodiments include identifying the one or more ligament attachment regions based on bony landmarks identified on the one or more images or volumetric data.

Figures 5A, 5B:
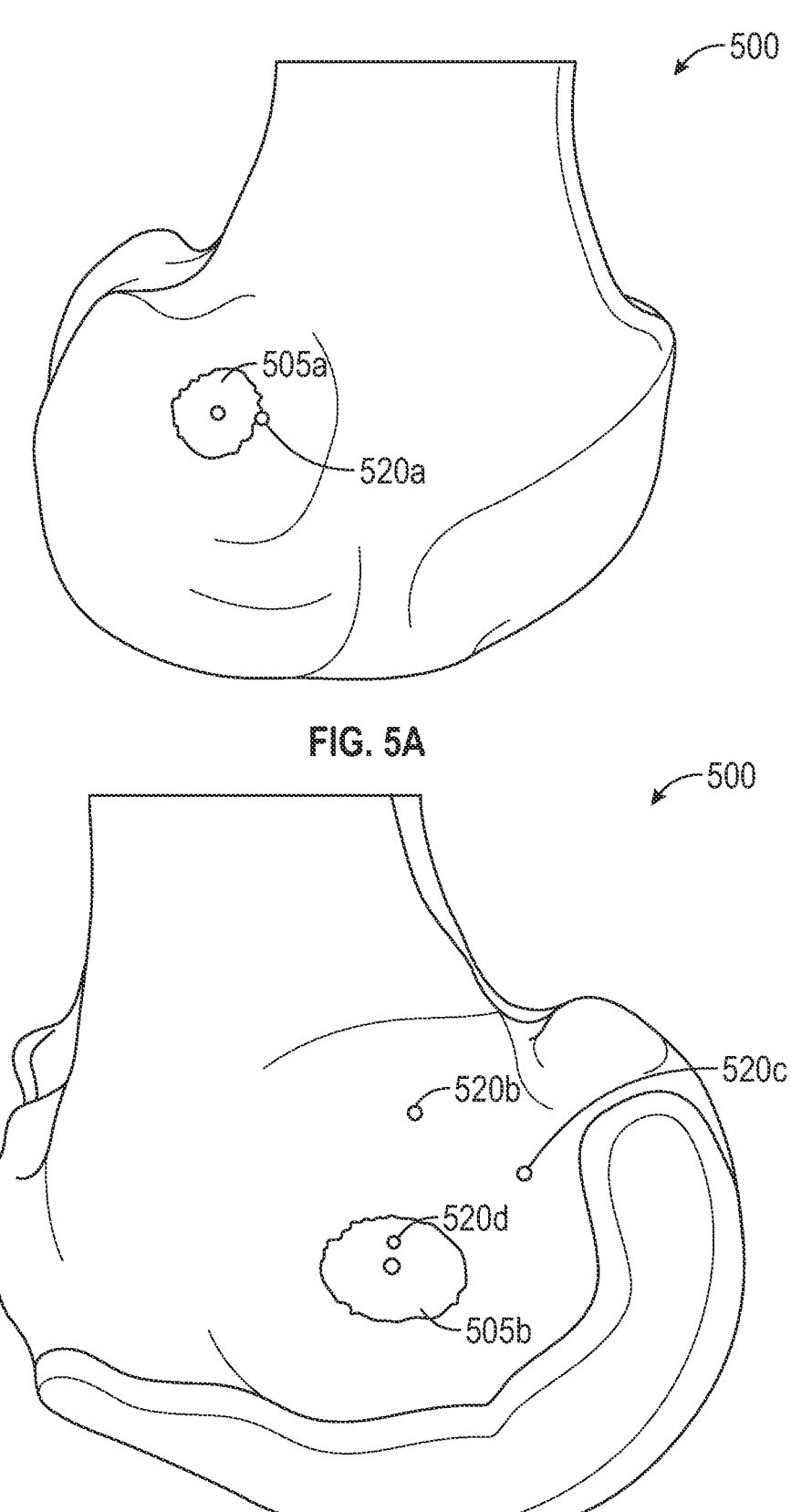
FIG. 5A illustrates a joint showing an example location of a lateral collateral ligament (LCL) attachment region with respect to a bony landmark, according to certain embodiments.
FIG. 5B illustrates the joint of FIG. 5A showing an example location of a medial collateral ligament (MCL) attachment region with respect to bony landmarks, according to certain embodiments.

FIG. 5A illustrates a joint 500 showing an example location of a LCL attachment region 505a with respect to a bony landmark 520a. For example, the location of the LCL 505a can be described/mapped (e.g., at a particular distance and direction) with respect to the lateral epicondyle 520a. FIG. 5B illustrates the joint 500 showing an example location of an MCL attachment region 505b with respect to bony landmarks 520b-d. For example, the location of the MCL 505b can be described/mapped with respect to the adductor tubercle 520b, gastrocnemius tubercle 520c, and medial epicondyle 520d. Therefore, in certain embodiments, together with the (e.g., average) dimensions of the ligament attachment region, an estimate can be made of the ligament attachment region and location.

In certain aspects, an attachment region may be a surface area on the bone where the ligament attaches to the bone. For example, an LCL attachment region and a MCL attachment region are shown on a femur in FIGS. 6A-6G.

Continuing, at block 406, one or more rotational axes of the joint implant are determined. For example, the joint implant may be a femoral component of a TKA implant. In certain embodiments, the information regarding the one or more rotational axes is provided by a manufacturer of the joint implant.

In certain embodiments, the one or more rotational axes of the joint implant are determined based on a digital representation (e.g., 2D or 3D) of the joint implant. For example, a digital representation of the joint implant may be generated based on images of the joint implant, such as using image processing module 208, may be obtained and stored (e.g., as an STL file) in image data store 206, etc. One or more geometric shapes, such as a circle, cylinder, sphere, etc., may then be fit to the digital representation of the joint implant, such as by image processing module 208 and/or analysis module 220. The one or more axes of rotation of the one or more geometric shapes (e.g., line perpendicular to circle and passing through center point of the circle, central/longitudinal axis of the cylinder, center of the sphere, etc.) may then be defined as the one or more rotational axes. For example, FIGS. 6A-6G illustrate a cylinder 625 shown as two circles fit to the femoral component 600, and the corresponding rotational axis 610 of the cylinder 625 is defined as the rotational axis 610 of the femoral component 600. Ligament attachment regions 605a (e.g., LCL attachment region) and 605b (e.g., MCL attachment region) are also illustrated.

In certain embodiments, multiple geometric shapes may be fit to the digital representation of the joint implant, such as one shape (e.g., cylinder) per condyle (e.g., the rotation axis may be a line connecting centers of gravity of the multiple shapes). In certain embodiments, multiple geometric shapes may be fit for multi-radius implants, to define a plurality of rotational axes.

Further, at block 408, a depiction of the joint and a depiction of the joint implant may be displayed on a computing device, such as overlaid. For example, visualization module 224 may render the depictions for display on display 304. For example, FIGS. 6A-6G illustrate an example rendering and display of a femoral component 600 as a joint implant, and a femur corresponding to a knee joint. In certain aspects, the visualization module 224 may render the joint as a whole including ligament(s) attached to the attachment region(s), such as based on user preference, as discussed.

In certain embodiments, the depiction of the joint and/or the depiction of the joint implant may be 2D, 3D, and/or 4D depictions. In certain embodiments, the depiction of the joint and/or the depiction of the joint implant may be schematic or lifelike depictions. In certain embodiments, the depiction of the joint and/or the depiction of the joint implant may be wireframe models, surface models, virtual models and/or volume models.

In certain embodiments, the depicted position of the joint implant relative to the joint may be determined or loaded from a pre-surgical plan accessible by the computing device. In certain embodiments, the visualization module 224 provides a user interface (UI) to allow a user to generate a pre-surgical plan, such as by choosing a size and/or position of the joint implant, and/or designating within at least one of the one or more depictions at least one position, wherein said position corresponds to a respective position relative to the joint. In certain embodiments, the visualization module 224 provides a UI to allow a user to modify a pre-surgical plan, such as by adjusting the size and/or position of the joint implant, and/or designating within at least one of the one or more depictions at least one position, wherein said position corresponds to a respective position relative to the joint intra-op (e.g., during surgery). The visualization module 224 may be equipped to run along with surgical navigation systems and devices including augmented reality fixed and/or mobile devices.

In certain embodiments, a user sets the position of the joint implant relative to the joint. In certain embodiments, as discussed, the computing device automatically selects a position of the joint implant relative to the joint.

In certain embodiments, the visualization module 224 also displays a visualization of the one or more rotational axes of the joint implant and/or the one or more ligament attachment regions, such as shown in FIGS. 6A-6G.

In certain embodiments, the position of the one or more rotational axes of the joint implant relative to the joint implant is loaded from a file accessible by visualization module 224. In certain embodiments, the position of the one or more rotational axes of the joint implant relative to the joint implant is determined from a digital representation of the one or more rotational axes, as discussed.

In certain embodiments, the position of the one or more ligament attachment regions relative to the joint is loaded from a file accessible by visualization module 224. In certain embodiments, the position of the one or more ligament attachment regions relative to the joint is determined based on segmentation, as discussed. In certain embodiments, the position of the one or more ligament attachment regions relative to the joint is determined based on bony landmarks, as discussed. In certain embodiments, the position of the one or more ligament attachment regions relative to the joint is determined based on a combination of one or more of a file, segmentation, and bony landmarks. In certain embodiments, the one or more ligament attachment regions may be displayed with a different color as compared to other elements displayed. In certain embodiments, an outer contour of the one or more ligament attachment regions is displayed.

Continuing, at block 414, a relative position of the one or more rotational axes of the joint implant with respect to the one or more ligament attachment regions is determined, such as an indicator for future ligament strains, as discussed. For example, it may be determined if a position of the one or more rotational axes align with (are within the area defined by) the one or more ligament attachment regions, such as by analysis module 220. In certain embodiments, an indication or warning (visual, audio, haptic, and/or the like) of whether a position of the one or more rotational axes align with (are within the area defined by) the one or more ligament attachment regions is presented to the user.

For example, in certain embodiments, a color, hatching, etc. of one or more of: the joint implant, one or more axes of rotation, one or more ligament attachment regions, etc., may be changed based on whether a position of the one or more rotational axes align with (are within the area defined by) the one or more ligament attachment regions is presented to the user. In certain embodiments, a degree to which the one or more rotational axes do or do not align is indicated, such as by the color, hatching, etc. being changed, based on how far and/or in which direction (e.g., anterior or posterior) or what distance outside or from center (e.g., center of gravity) of the one or more areas of the one or more ligament attachment regions the one or more axes of rotation lie (e.g., one or more points on the one or more axes of rotation closest to the one or more ligament attachment regions). For example, the direction in which the one or more areas of the one or more ligament attachment regions do not align with the one or more rotational axes may help indicate whether an anterior or posterior position of the attachment could result in stress in the ligament, and provides more information than just the amount of difference in alignment alone.

In certain embodiments, whether the one or more rotational axes align with (are within the area defined by) the one or more ligament attachment regions is computed using known techniques in the art, such as checking whether each of the one or more rotational axes pass through a polygon (e.g., 2D or 3D polygon) corresponding to the one or more ligament attachment regions.

In certain aspects, artificial intelligence, such as machine learning, may be used to learn about attachment regions over time, such as based on patient data and implant sizes chosen from an implant directory over time, and make appropriate suggestions to a user. For example, block 404 may be performed using machine learning, such that identification of ligament attachment regions is improved over time. In certain aspects, machine learning may be used to suggest a particular implant size, type, etc., based on the identified ligament attachment regions. In certain aspects, machine learning may be used to suggest implant size, type, etc., based on surgeon history.

In certain embodiments, a given ligament may have multiple ligament attachment regions, and a relative position of the one or more rotational axes of the joint implant with respect to the multiple ligament attachment regions of the ligament is determined. For example, if a rotation of a first ligament attachment area around the one or more rotational axes (e.g., corresponding to natural movement of the joint, such as flexion) increases a distance between the two attachment areas, the computing device may provide an indication or warning (visual, audio, haptic, and/or the like) to the user, such as indicating that such increasing distance may increase future ligament strains (e.g., risk of excessive ligament stresses or need for ligament releases during surgery). In certain embodiments, the computing device may provide an indication (visual, audio, haptic, and/or the like) to the user, such as identifying which ligaments need to be released. In another example, if a rotation of a first ligament attachment area around the one or more rotational axes (e.g., corresponding to natural movement of the joint, such as flexion) decreases a distance between the two attachment areas, the computing device may provide an indication or warning (visual, audio, haptic, and/or the like) to the user, such as indicating that such decreasing distance may decrease future ligament strains (e.g., risk of joint instability). In certain embodiments, for a given ligament having multiple ligament attachment regions, a center of gravity of the multiple ligament attachment regions is determined, and a distance between the attachment areas is computed as the distance between the centers of gravity.

In certain embodiments, areas that lead to increased future ligament strains when one or more rotation axes pass through them (e.g., in flexion) are depicted, such as using coloring, hatching, etc. to depict such areas. For example, increased ligament strains can result from an anterior and/or proximal location of the rotation axis with respect to the ligament attachment region.

In certain embodiments, areas that lead to decreased future ligament strains when one or more rotation axes pass through them (e.g., in flexion) are depicted, such as using coloring, hatching, etc. to depict such areas. For example, decreased ligament strains can result from a misalignment of the rotation axis with respect to both the medial and lateral ligaments, or a misbalance between the medial and lateral sides.

FIG. 7 depicts an example visualization of a joint 700 used to determine the location of the rotational axis 710 of the femoral component with respect to the collateral ligament attachment regions 705. Based on the techniques discussed herein, the femoral component was considered to be misaligned when either 1) the axis 710 intersected more than 2 mm (depicted as circle 715) from the LCL or MCL attachment 705 in anterior and/or proximal direction or 2) the axis 705 intersected more than 2 mm from the attachment 705 for both LCL and MCL in any direction. Accordingly, techniques discussed herein can identify misalignments of joint implants.

In certain embodiments, as discussed, if the computing device indicates that a position of the one or more rotational axes do not align with the one or more ligament attachment regions, a user or the computing device automatically may change/adjust a position of the joint implant relative to the joint and the blocks 408 and 410 may be repeated, such as iteratively. In certain aspects, a user or the computing device automatically may change/adjust a position of the joint implant relative to the joint even if the computing device indicates that a position of the one or more rotational axes aligns with the one or more ligament attachment regions, such as to achieve better alignment, such as toward the center (e.g., of gravity) of the one or more ligament attachment regions. Accordingly, embodiments herein provide for improved visualization and pre-operative planning of joint implant surgery be allowing for better positioning of a joint implant relative to a joint.

It should be noted that in certain embodiments, one or more of the methods described herein is a computer-implemented method. Further, certain steps may be performed automatically, manually by a user of a computing device, or partially manually and partially automatically such as based on input from a user of a computing device.

Further, in certain embodiments, a person, such as a clinician, engineer, technician, medical professional, a trainer etc., may use a computing device to, or the computing device itself may automatically perform one or more steps of one or more methods described herein.

It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims. Further, one or more blocks/steps may be removed or added.

Various embodiments disclosed herein provide for the use of a computer system to perform certain features. A skilled artisan will readily appreciate that these embodiments may be implemented using numerous different types of computing devices, including both general-purpose and/or special-purpose computing system environments or configurations. Examples of well-known computing systems, environments, and/or configurations that may be suitable for use in connection with the embodiments set forth above may include, but are not limited to, personal computers, server computers, hand-held or laptop devices, multiprocessor systems, microprocessor-based systems, programmable consumer electronics, network PCs, minicomputers, mainframe computers, distributed computing environments that include any of the above systems or devices, and the like. These devices may include stored instructions, which, when executed by a microprocessor in the computing device, cause the computer device to perform specified actions to carry out the instructions. As used herein, instructions refer to computer-implemented steps for processing information in the system. Instructions can be implemented in software, firmware or hardware and include any type of programmed step undertaken by components of the system.

A microprocessor may be any conventional general-purpose single- or multi-chip microprocessor such as a Pentium® processor, a Pentium® Pro processor, a 8051 processor, a MIPS® processor, a Power PC® processor, or an Alpha® processor. In addition, the microprocessor may be any conventional special-purpose microprocessor such as a digital signal processor or a graphics processor. The microprocessor typically has conventional address lines, conventional data lines, and one or more conventional control lines.

Aspects and embodiments of the inventions disclosed herein may be implemented as a method, apparatus or article of manufacture using standard programming or engineering techniques to produce software, firmware, hardware, or any combination thereof. The term "article of manufacture" as used herein refers to code or logic implemented in hardware or non-transitory computer readable media such as optical storage devices, and volatile or non-volatile memory devices or transitory computer readable media such as signals, carrier waves, etc. Such hardware may include, but is not limited to, field programmable gate arrays (FPGAs), application-specific integrated circuits (ASICs), complex programmable logic devices (CPLDs), programmable logic arrays (PLAs), microprocessors, or other similar processing devices.

What is claimed is:

1. A computer-implemented method of evaluating placement of a joint implant with respect to a joint, the method comprising:
   determining one or more ligament attachment regions of the joint;
   determining one or more rotational axes of the joint implant, wherein each of the one or more rotational axes of the joint implant is a rotational axis about which the joint implant is configured to rotate after implantation;
   determining a position of the joint implant relative to the joint;
   determining whether the one or more rotational axes fall within or outside of the one or more ligament attachment regions when the joint implant is at the position;
   displaying a depiction of the joint implant relative to the joint at the position;
   displaying an indication that the one or more rotational axes fall outside of the one or more ligament attachment regions when the joint implant is at the position;
   determining an adjusted position of the joint implant relative to the joint when the one or more rotational axes do not fall within the one or more ligament attachment regions when the joint implant is at the position;
   displaying an updated depiction of the joint implant relative to the joint at the adjusted position; and
   displaying an indication that the one or more rotational axes fall within the one or more ligament attachment regions when the joint implant is at the adjusted position.

2. The method of claim 1, wherein determining the one or more ligament attachment regions of the joint comprises:
   obtaining one or more images or volumetric data of the joint; and
   segmenting the one or more images or volumetric data of the joint to identify the one or more ligament attachment regions.

3. The method of claim 1, wherein determining the one or more ligament attachment regions of the joint comprises:
   obtaining one or more images or volumetric data of the joint; and
   identifying the one or more ligament attachment regions based on bony landmarks identified on the one or more images or volumetric data.

4. The method of claim 1, wherein determining the one or more rotational axes of the joint implant comprises fitting one or more geometric shapes to the joint implant.

5. The method of claim 4, wherein the one or more geometric shapes comprise one or more cylinders, circles, or spheres.

6. The method of claim 1, further comprising:
   determining whether a distance between multiple ligament attachment regions of a single ligament changes during flexion of the joint when the joint implant is at the position; and
   displaying an indication of whether the distance changes.

7. The method of claim 1, further comprising:
   determining a direction in which the one or more ligament attachment regions do not align with the one or more rotational axes; and
   displaying an indication of the direction.

8. A computing device comprising:
   a memory; and a processor coupled to the memory, the processor and memory configured to perform operations for evaluating placement of a joint implant with respect to a joint, the operations comprising:

determining one or more ligament attachment regions of the joint;

determining one or more rotational axes of the joint implant, wherein each of the one or more rotational axes of the joint implant is a rotational axis about which the joint implant is configured to rotate after implantation;

determining a position of the joint implant relative to the joint;

determining whether the one or more rotational axes fall within or outside of the one or more ligament attachment regions when the joint implant is at the position;

displaying a depiction of the joint implant relative to the joint at the position;

displaying an indication that the one or more rotational axes fall outside of the one or more ligament attachment regions when the joint implant is at the position;

determining an adjusted position of the joint implant relative to the joint when the one or more rotational axes do not fall within the one or more ligament attachment regions when the joint implant is at the position;

displaying an updated depiction of the joint implant relative to the joint at the adjusted position; and displaying an indication that the one or more rotational axes fall within the one or more ligament attachment regions when the joint implant is at the adjusted position.

9. The computing device of claim 8, wherein determining the one or more ligament attachment regions of the joint comprises:

obtaining one or more images or volumetric data of the joint; and segmenting the one or more images or volumetric data of the joint to identify the one or more ligament attachment regions.

10. The computing device of claim 8, wherein determining the one or more ligament attachment regions of the joint comprises:

obtaining one or more images or volumetric data of the joint; and identifying the one or more ligament attachment regions based on bony landmarks identified on the one or more images or volumetric data.

11. The computing device of claim 8, wherein determining the one or more rotational axes of the joint implant comprises fitting one or more geometric shapes to the joint implant.

12. The computing device of claim 11, wherein the one or more geometric shapes comprise one or more cylinders, circles, or spheres.

13. The computing device of claim 8, wherein the operations further comprise:

determining whether a distance between multiple ligament attachment regions of a single ligament changes during flexion of the joint when the joint implant is at the position; and displaying an indication of whether the distance changes.

14. The computing device of claim 8, wherein the operations further comprise:

determining a direction in which the one or more ligament attachment regions do not align with the one or more rotational axes; and displaying an indication of the direction.

15. A non-transitory computer-readable medium having computer-executable instructions stored thereon, which, when executed by a processor of a computing device, cause the computing device to perform operations for evaluating placement of a joint implant with respect to a joint, the operations comprising:

determining one or more ligament attachment regions of the joint;

determining one or more rotational axes of the joint implant, wherein each of the one or more rotational axes of the joint implant is a rotational axis about which the joint implant is configured to rotate after implantation;

determining a position of the joint implant relative to the joint;

determining whether the one or more rotational axes fall within or outside of the one or more ligament attachment regions when the joint implant is at the position;

displaying a depiction of the joint implant relative to the joint at the position;

displaying an indication that the one or more rotational axes fall outside of the one or more ligament attachment regions when the joint implant is at the position;

determining an adjusted position of the joint implant relative to the joint when the one or more rotational axes do not fall within the one or more ligament attachment regions when the joint implant is at the position;

displaying an updated depiction of the joint implant relative to the joint at the adjusted position; and displaying an indication that the one or more rotational axes fall within the one or more ligament attachment regions when the joint implant is at the adjusted position.

16. The non-transitory computer-readable medium of claim 15, wherein determining the one or more ligament attachment regions of the joint comprises:

obtaining one or more images or volumetric data of the joint; and segmenting the one or more images or volumetric data of the joint to identify the one or more ligament attachment regions.

17. The non-transitory computer-readable medium of claim 15, wherein determining the one or more ligament attachment regions of the joint comprises:

obtaining one or more images or volumetric data of the joint; and identifying the one or more ligament attachment regions based on bony landmarks identified on the one or more images or volumetric data.

18. The non-transitory computer-readable medium of claim 15, wherein determining the one or more rotational axes of the joint implant comprises fitting one or more geometric shapes to the joint implant.

* * * * *